(12) United States Patent
Boland et al.

(10) Patent No.: US 7,065,243 B2
(45) Date of Patent: Jun. 20, 2006

(54) METHOD AND SYSTEM FOR CREATING DENTAL MODELS FROM IMAGERY

(75) Inventors: John T. Boland, Fairport, NY (US); John P. Spoonhower, Webster, NY (US); John R. Squilla, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 760 days.

(21) Appl. No.: 09/894,627

(22) Filed: Jun. 28, 2001

(65) Prior Publication Data

US 2003/0012423 A1    Jan. 16, 2003

(51) Int. Cl.
G06K 9/00    (2006.01)

(52) U.S. Cl. .................. 382/154; 345/420; 433/223

(58) Field of Classification Search ............ 382/182, 382/154; 345/420, 646
See application file for complete search history.

(56) References Cited

U.S. PATENT DOCUMENTS

| | | | |
|---|---|---|---|
| 4,837,732 A | 6/1989 | Brandestini et al. | ... 364/413.28 |
| 5,273,429 A | 12/1993 | Rekow et al. | ............... 433/215 |
| 5,372,502 A | 12/1994 | Massen et al. | .............. 433/215 |
| 5,452,219 A | 9/1995 | Dehoff et al. | .......... 364/474.05 |
| 5,851,115 A | 12/1998 | Carlsson et al. | ............. 433/215 |
| 5,857,853 A | 1/1999 | van Nifterick et al. | ...... 433/213 |
| 6,068,482 A * | 5/2000 | Snow | ......................... 433/223 |
| 6,512,994 B1 * | 1/2003 | Sachdeva | .................... 702/167 |
| 6,648,640 B1 * | 11/2003 | Rubbert et al. | ............... 433/24 |

FOREIGN PATENT DOCUMENTS

WO    WO 01/80763 A2    4/2001

OTHER PUBLICATIONS

Williamson, James R. What is Photogrammetry? [online]. © 1999-2000. [retrieved on Jun. 30, 2004]. Retrieved from the Intern <URL:http://www.123photogrammetry.com/photogrammetry.html>.*

U.S. Appl. No. 09/796,239, filed Feb. 28, 2001, John P. Spoonhower et al.

(Continued)

Primary Examiner—Vikkram Bali
Assistant Examiner—Wes Tucker
(74) Attorney, Agent, or Firm—David M. Woods; Nelson Adrian Blish

(57) ABSTRACT

Creating a dental model from a series of images of an intra-oral object includes the steps of (a) capturing a series of images of an intra-oral object from a plurality of capture positions, where the object includes common surface features and a control target arranged with respect to the object to provide control features; (b) measuring the common features from the series of images of the object and the control features from the control target imaged with the images of the object; (c) analytically generating a 3-dimensional model of the object by photogrammetrically aligning the measurements of the control features, thereby reducing image errors due to the variability of the capture positions; and (d) adjusting the photogrammetrically aligned 3-dimensional model of the object by aligning the common features of the model to like features on the image of the object, thereby producing an aligned dental model from the series of images.

17 Claims, 3 Drawing Sheets

OTHER PUBLICATIONS

"Automatic Creation of 3D Facial Models" by Takaaki Akimoto and Yasuhito Suenaga, IEEE Computer Graphics & Applications, pp. 16-22.

"Synthesizing Realistic Facial Expressions form Photographs" by Frederic Pighin, Jamie Hecker, Dani Lischinski, Richard Szeliski, David H. Salesin. Computer Graphics Proceedings, Annual Conference Series, 1998, pp. 75-83.

"Manual of Photogrammetry", Fourth Edition. Chester C. Slama, Editor-in-Chief. American Society of Photogrammetry, 1980, pp. 77-88.

* cited by examiner

METHOD AND SYSTEM FOR CREATING DENTAL MODELS FROM IMAGERY

FIELD OF THE INVENTION

The invention relates generally to the field of dental imagery, and in particular to a method and apparatus for effecting imagery of a prepared cavity in a tooth followed by automatic generation of a model to control automatic fabrication of a dental inlay for the cavity.

BACKGROUND OF THE INVENTION

The invention described herein relates generally to the following conventional situation. A dentist prepares a cavity of a decayed tooth to allow its restoration by means, e.g., of an inlay or a crown. After the preparation has been rendered, an impression of the cavity is taken, and is ordinarily sent to a dental laboratory. Contrary to such conventional techniques, there are different and more recent techniques which alleviate the role of the dental laboratory and fabricate the desired restorative piece in the dental office. In particular, the prepared cavity is registered by an electro-optic scan head. The data thus obtained can be complemented by operator input, using techniques from the CAD (Computer-Aided-Design) domain, and the final piece is fabricated with the aid of a miniature NC (numerical control) grinding machine.

U.S. Pat. No. 4,837,732 (Brandestini et al) describes a method for a dentist to record the shape in situ of teeth prepared for repair. The method involves the acquisition of data defining the three-dimensional shape of prepared teeth and their immediate vicinity. First, a video display shows a live image from a scan head, and the scan head is manually oriented relative to the prepared teeth while observing the image of the teeth on the video display. Thereafter the data produced by the scan head in a selected orientation generates corresponding depth and contrast images, and a depth image is processed based on the contrast image. This method also includes the step of superimposing graphic markers on the image displayed on the video display to facilitate an on-line alignment of the teeth displayed in the live image with reference data from previous data acquisitions.

The drawback to this method from the prior art is that it incorporates a registration scheme that can later interfere with the quality of the results, and also requires that the dentist be able to hold the scan head almost perfectly still at a specific point in the procedure. More specifically, the artifacts typically due to the 3D registration scheme (such as fringe, speckle and/or venetian blind effect) are cited in the patent as "intolerable and must be eliminated" since phase angle differences are used for measurement of the depth. Furthermore, the patent cites a need for a "quasi-instantaneous 3D acquisition following a trigger release", the essential condition being that the orientation of the scan head must not change between the search and acquisition modes.

What happens in Brandestini et al is that the 3D result is overlaid on the search image allowing the dentist to verify the result. What is needed, however, is a system in which the 3D results are projected into the image using the projective equations of photogrammetry. This would cause the results to appear as if they were actually present in the scene at the time of image acquisition, allowing a much more accurate and precise evaluation.

Previous photogrammetric-based approaches, however, (see, e.g., U.S. Pat. No. 5,372,502) have not been too successful for a number of reasons. For example, such approaches have not been successful because it is hard to determine the exact relationship between the camera and the object. Moreover, it is also hard to precisely measure the object because teeth are fairly uniform in color and have little texture (which is in part why it is hard to determine the relationship discussed above).

SUMMARY OF THE INVENTION

The present invention is directed to overcoming one or more of the problems set forth above. Briefly summarized, according to one aspect of the present invention, a method (and system) for creating a dental model from a series of images of an intra-oral object includes the steps of (a) capturing a series of images of the intra-oral object from a plurality of capture positions, where the object includes common surface features and a control target arranged with respect to the object to provide control features; (b) measuring the control features from the control target imaged with the images of the object; (c) analytically generating a 3-dimensional model of the object by photogrammetrically aligning the measurements of the control features, thereby providing a photogrammetrically-aligned 3-dimensional model of the object while reducing image errors due to the variable orientation of the capture positions; and (d) adjusting the photogrammetrically aligned 3-dimensional model of the object by aligning the common features of the model to like features on the image of the object, thereby producing an aligned dental model from the series of images. In practice, the last stage involves the application of a 3-dimensional morphing algorithm to correct for the misalignment.

The principal advantage of the invention is that the use of photogrammetric projection methods and adjustment to control eliminates the need for a registration scheme, such as that used in Brandestini et al, which projects stripes of light onto the target and can result in unacceptable artifacts. Furthermore, under the present invention, there is no need to restrict the acquisition of the image(s) to a "quasi-instantaneous" state, as phase information is not used.

It becomes possible to measure the exact relationship between the camera and the intra-oral object because the use of a target provides something to measure, thus allowing the determination of the relationship between the camera and target. The use of 3D morphing addresses the matter of precisely measuring the object itself by projecting the data that is available into the picture and letting one see how well it fits—in the 3D object space. If correct, the model of the tooth should "fit" the tooth "skin tight".

These and other aspects, objects, features and advantages of the present invention will be more clearly understood and appreciated from a review of the following detailed description of the preferred embodiments and appended claims, and by reference to the accompanying drawings.

DETAILED DESCRIPTION OF THE INVENTION

Because dental image processing systems and methods are well known, the present description will be directed in particular to elements forming part of, or cooperating more directly with, apparatus and method in accordance with the present invention. Elements not specifically shown or described herein may be selected from those known in the art. Certain aspects of the embodiment to be described may be provided in software. Given the system as shown and described according to the invention in the following materials, software not specifically shown, described or suggested herein that is useful for implementation of the invention is conventional and within the ordinary skill in such arts. This is particularly true given the advanced technical state of conventional photogrammetry and the well-understood current automation of the photogrammetric process.

Figure 4:
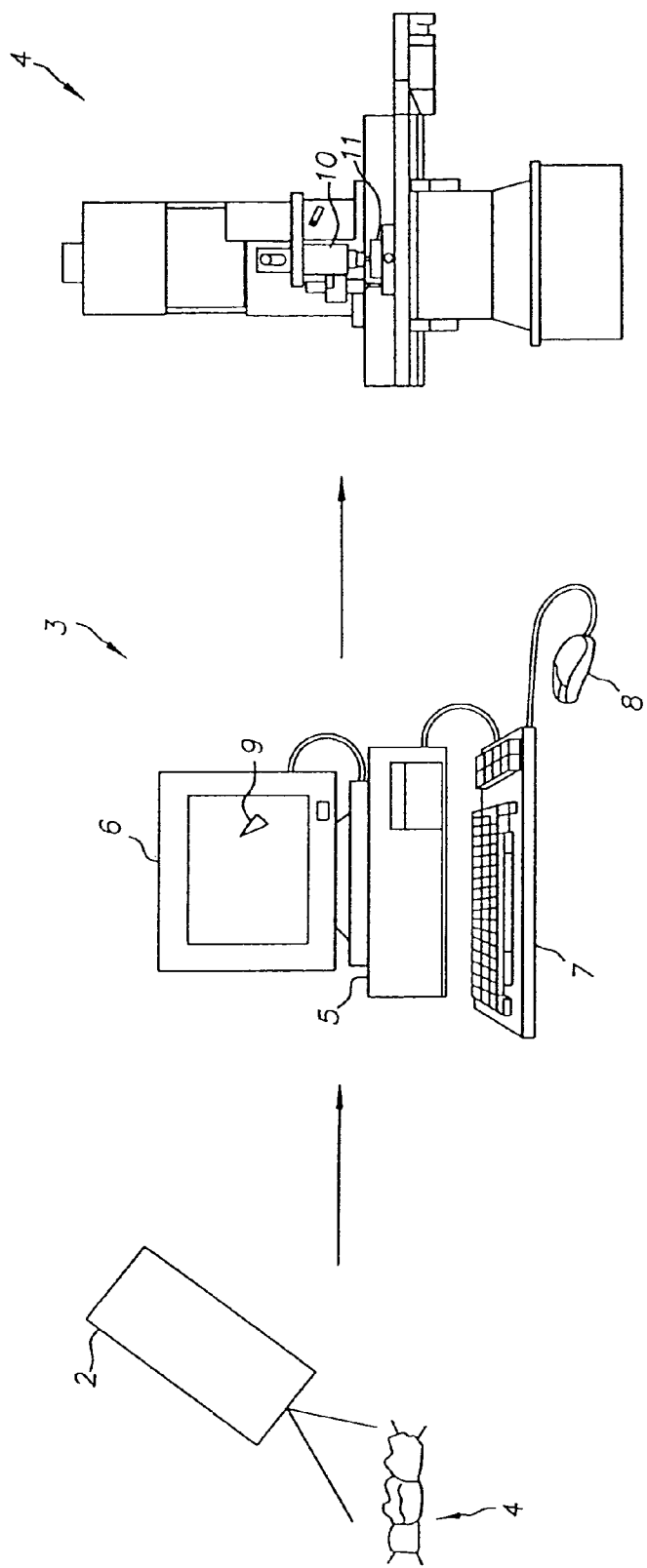
FIG. 4 is a diagram of a dental system that utilizes the method shown in FIG. 1.

Referring initially to FIG. 4, a preferred embodiment of the invention is implemented in a system including an intra-oral camera 2, a computer system 3 including instructions for implementing the invention and a machine tool 4. In the schematic shown in FIG. 4, it should be understood that the interconnections between the camera 2, the computer system 3 and the machine tool 4 are shown by arrows, and therefore not specifically indicated. These interconnections may take various forms, such as a cable or any other electromagnetic connection (such as an rf transmission), or the manual transfer of data from machine to machine. The camera 2 may be any type of conventional dental camera that is capable of capturing a reasonably high resolution image of an intra-oral object, such as the teeth 4; a preferred example is the intra-oral camera disclosed in commonly assigned, copending U.S. patent application Ser. No. 09/796,239, entitled "Intra-Oral Camera with Integral Display", filed Feb. 28, 2001 in the names of J. P. Spoonhower, J. R. Squilla and J. T. Boland, and which is incorporated herein by reference.

The camera 2 is hand held by the dentist and several images are captured of the teeth; it is understood, however, that the orientation of the camera relative to the teeth will vary from one image to the next. The elimination of the effect of these different orientations on the subsequent measurements is one feature of the invention. The digitized data from the camera 2 is transferred to the computer system 3 for processing. The methodology of the invention is implemented by the computer system 3 in its processor 5, and the imaging results may be interactively displayed on a monitor 6. An operator using a keyboard 7 and/or a mouse 8 can manipulate a cursor 9 to perform measurements of the type that will be subsequently described. The output from the computer system 3 is a digitized three-dimensional surface pattern that is transferred to the machine tool 4 as a tool path program for the fabrication of a dental mold or a restorative piece. The program will direct a milling cutter 10 in the milling of the tooth mold or the restorative piece 11 from a suitable substrate, for example, ceramic or any other suitable machinable material.

The dental imaging method according to the invention employs a mensuration method that utilizes photogrammetric projection, analytical adjustment to control and three-dimensional morphing to develop accurate dental models. Mensuration, in this instance, refers to a measurement process involving several steps: (1) the identification of control points on the digitized image, (2) the stereoscopic transfer of those points to the overlapping images upon which they appear, and (3) the actual measurement of the image coordinates of the control points.

Photogrammetry generally is the science of measuring graphically by means of light, and more specifically the science of obtaining reliable measurements by means of photographs or other forms of imagery, such as electronic sensing by a sensor (see generally *Manual of Photogrammetry, Fourth Edition*, American Society of Photogrammetry, 1980). Photogrammetric projection refers to an image projection that uses an analytical representation of the physical model that describes the imaging process of the sensor. The term projection specifically refers to the concept of a light ray projecting from the intra-oral object, through the sensor lens, to the image plane, in this case using the physical model of the imaging process to determine where the points will be located.

Analytical adjustment to control refers to the process of correcting the set of parameters which describe the physical model, to a subset of known, or control, parameters. A least squares adjustment process is typically applied to a set of normal equations, derived from a set of linearized condition equations, which in turn are partial derivatives of the image coordinates with respect to the total parameter set. Details of the least squares process is well known to those of ordinary skill in this art and described, e.g., in the *Manual of Photogrammetry, Fourth Edition*, op. cit., pp. 77–88, which is incorporated herein by reference.

Three-dimensional morphing refers to the process of adjusting a 3-dimensional, object model to an image(s) of the object. This is accomplished by projecting a hypothesized 3-dimensional model of the object into an existing image (through the analytical physical model referred to above), detecting the misalignment between the true image and the projected, object model-derived image, and making corrections to the object model (which is then re-projected) to improve the fit. Techniques for three-dimensional morphing are well known in the art and will not be described in detail herein. For further information, reference may be made to articles by Frederic Pighin et al., "Synthesizing Realistic Facial Expressions from Photographs", in *Computer Graphics Proceedings, Annual Conference Series*, 1998, pp. 75–83 and by Takaaki Akimoto et al., "Automatic Creation of 3D Facial Models", in *IEEE Computer Graphics & Applications*, September 1993, pp. 16–22. In these articles, the specifics are directed toward facial models, but the technology application to teeth models would be the same.

Figure 1:
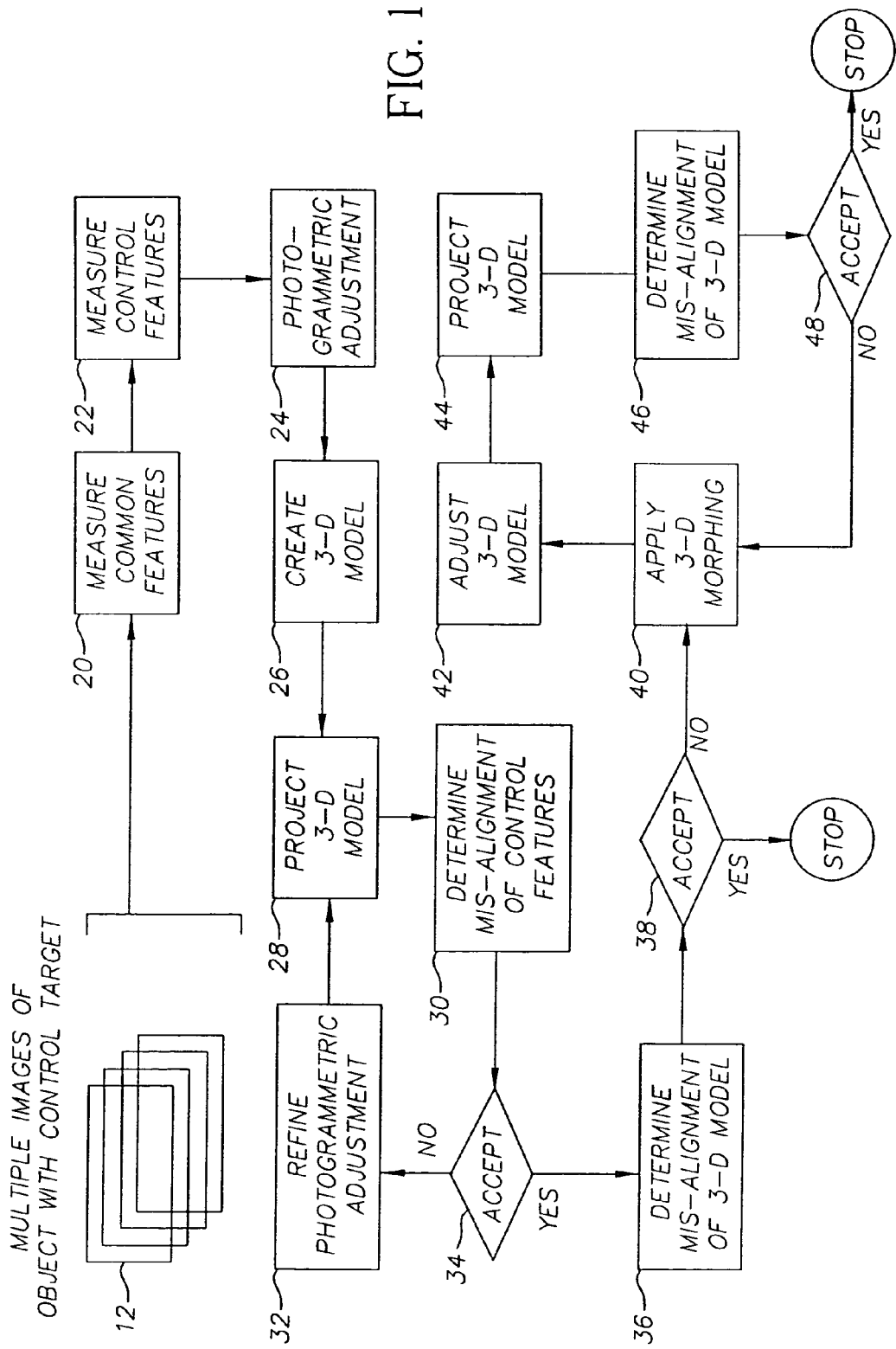
FIG. 1 is a block diagram of the method for creating dental models from imagery according to the invention.
Figure 2:
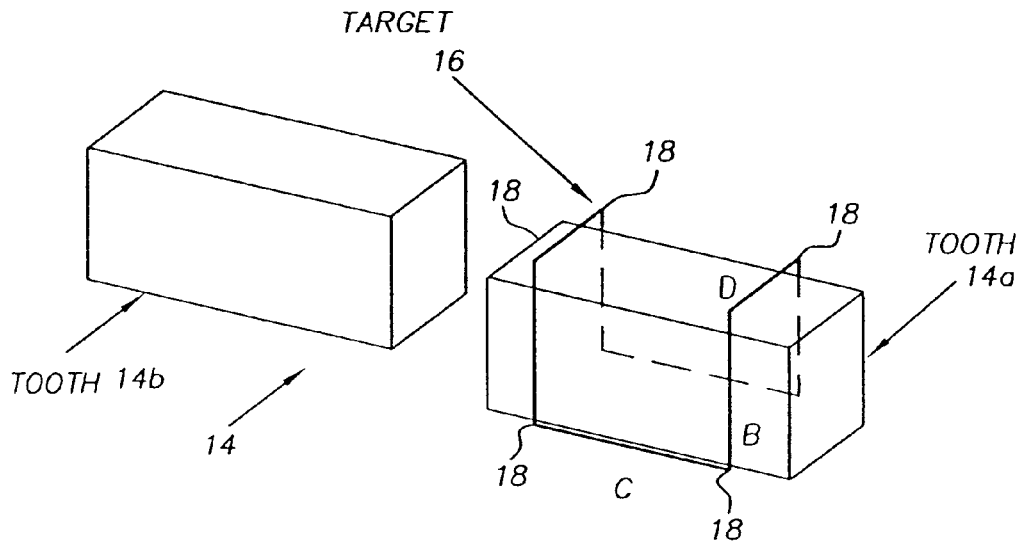
FIG. 2 is a perspective diagram of a target useful with the method described in FIG. 1.

Referring to FIGS. 1 and 2, the method according to the invention is shown, in which multiple images 12 of an intra-oral object (one or more teeth 14) are initially captured from several different aspects and/or positions by the camera 2. For each image, one or more of the teeth 14 (e.g., a tooth 14a) includes a control target 16, as shown in FIG. 2. (In practice, the tooth is typically either the original, unprepared tooth or the tooth as prepared (i.e., a tooth stump) for the restorative procedure.) The target 16 is rigid material, of saddle form, which rests on the tooth 14a with length C along the side of the tooth. (Although not shown as such in FIG. 2, the control target 16 could span several teeth, such as both teeth 14a and 14b.) Lengths A, B, C, and D are known, and may be unequal. Angles included by the vertices 18 are also known; as will be described, the vertices 18 are the aforementioned known, or control, parameters that are used in the analytical adjustment to control. Several targets may be constructed in varying sizes to accommodate different size teeth. Generally, several images are taken from several different aspects/positions as the basis for a 3-dimensional view of the intra-oral object, including both the control parameters and certain common features on the tooth, such as the cusps and valleys describing the natural topographic surface of the tooth (or the tooth stump, if the intra-oral object is a prepared tooth).

The mensuration process involves the measurement of common features or parameters (the cusps and valleys) in a feature measurement stage 20 and the measurement of control features or parameters (the vertices 18) on the target 16 in a control measurement stage 22. There are several ways to take these measurements. Referring to FIG. 4, these measurements may be interactively taken by an operator positioning the cursor 9 over the respective features on each of the multiple images 12 as they are displayed on the monitor 6; the coordinates of each measurement are then captured by the processor 5. Alternatively, the processor 5 may employ appropriate conventional image processing algorithms to automatically locate each of the features; this may involve image enhancement and other feature improvement algorithms, as necessary. The measurements are then processed in a photogrammetric adjustment stage 24 in order to compute the object-space coordinates of any object point which is imaged in the multiple overlapping images from varying camera orientations; this process utilizes the aforementioned least squares process described in the *Manual of Photogrammetry, Fourth Edition*, op. cit. Basically, this is a multiray stereo intersection process that is used to locate each image point relative to the camera position. The result is a 3-dimensional model 26 of the tooth that has been processed with an analytical representation of the physical model which represents the imaging process of the sensor that captured the images.

However, the imaging device is usually a handheld camera that does not make a perfect geometric representation of the object, which creates errors due to the lack of certainty of knowledge about the image positions. One of the features of the invention is to tackle the problem of eliminating these errors, i.e., the camera's variability in orientation, before attempting to correct for errors in the actual model of the tooth. In this manner, the requirement (and problem) noted in the prior art, namely, that the scan head or imaging device must be held perfectly still, can be avoided. Therefore, an analytical adjustment using the control points (the vertices 18) to correct the estimates is made by analytically projecting the 3-D model 26 in an analytical projection stage 28 into an existing image (one of the multiple images 12), determining the misalignment of the control points (the vertices 18) between the model and the image in a misalignment stage 30 and refining the photogrammetric adjustments in a refinement stage 32 if the misalignment is unacceptable (decision 34). The projection is an analytical process, meaning that it is accomplished mathematically, and the determination of misalignment may be accomplished interactively (by using the cursor 9) or automatically with appropriate image processing algorithms. It is helpful to understand that this projection process utilizes the physical model representing the imaging process, therefore differing from a simple overlay of the 3-D model onto the image. Once these corrections are made, the variability in the model caused by the various camera orientations is reduced to an acceptable level, if not eliminated.

Once the control alignment is acceptable, the slopes and curves between the cusps and valleys in the model should either match, or be made to match, the corresponding features in the image of the tooth. Thus, it is necessary to determine the remaining misalignment of the model relative to the actual image in a misalignment determination stage 36, that is, to determine the misalignment (if any) of the common features in the model with respect to the same features in the actual image. If misalignment is present (decision 38), a three-dimensional morphing stage 40 is initiated for adjusting the 3-dimensional object model in an adjustment stage 42 to an image(s) of the object. (This changes the 3-dimensional position of points in the model without affecting the prior alignment adjustment regarding the camera orientation.) This is accomplished in a projection stage 44 by projecting the hypothesized 3-dimensional model of the object into one of the existing images (through the analytical physical model referred to above) of the intra-oral object. Then, the misalignment between the true image and the projected, object model-derived image is detected in a misalignment stage 46. If the misalignment is acceptable (decision 48), the process is ended; otherwise, corrections are made to the object model in the stages 40 and 42 (which is then re-projected) to improve the fit.

At this point, an acceptable model of the tooth has been generated and may be used in subsequent processing, such as in the fabrication of the desired restorative piece, either in a laboratory or in the dental office by use of the machine tool 4. It should be understood that in addition to teeth, other dental prosthetics can be modeled in accordance with the invention, including without limitation bridges, veneers and other dental restorative units. Moreover, various other types of fabrication may be employed without limitation in addition to milling or cutting, such as injection molding.

Figure 3:
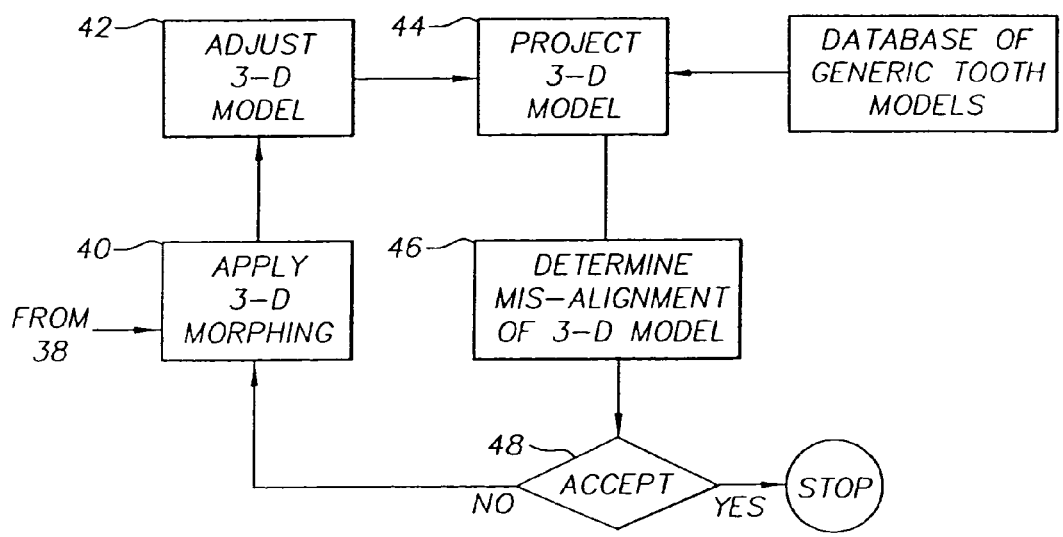
FIG. 3 is a block diagram of a morphing technique utilizing a database of generic tooth models.

FIG. 3 represents an alternative method for adjusting the 3-dimensional object model to an image(s) of the intra-oral object, that is, an alternative method to the logic represented by the elements 40–48 of FIG. 1. More specifically, in the alternative approach of FIG. 3, generic 3D models from a database 50 of such items may be used in addition to, or as a substitute for the 3D model provided in the elements 40–48. This approach specifically addresses the issue around difficulty in accurately measuring the cusps and valleys, as they may not be as well defined as the target vertices, by allowing a generic tooth model to be used instead. This essentially means that in FIG. 1, the 3-D model 26 can be eliminated, or more correctly, reduced to only creating a 3D model of the target (vs. the tooth and target) and proceeding from there.

The invention has been described with reference to a preferred embodiment. However, it will be appreciated that variations and modifications can be effected by a person of ordinary skill in the art without departing from the scope of the invention.

| PARTS LIST | |
|---|---|
| 2 | camera |
| 3 | computer system |
| 4 | machine tool |
| 5 | processor |
| 6 | monitor |
| 7 | keyboard |
| 8 | mouse |
| 9 | cursor |
| 10 | milling cutter |
| 11 | restorative piece |
| 12 | multiple images |
| 14 | teeth |
| 14a | tooth |
| 14b | tooth |
| 16 | control target |
| 18 | vertices |
| 20 | feature measurement stage |

-continued

PARTS LIST

| | | |
|---|---|---|
| 22 | control measurement stage | |
| 24 | photogrammetric stage | |
| 26 | 3-D model | |
| 28 | projection stages | |
| 30 | misalignment stage | |
| 32 | refinement stage | |
| 34 | decision | |
| 36 | misalignment stage | |
| 38 | decision | |
| 40 | 3-D morphing stage | |
| 42 | adjustment stage | |
| 44 | projection stage | |
| 46 | misalignment stage | |
| 48 | decision | |
| 50 | database of 3-D models | |

What is claimed is:

1. A method for creating a dental model from image parameters obtained from a series of overlapping images of an intra-oral object, said method comprising the steps of:
   (a) capturing the series of overlapping images of the intra-oral object and a 3-dimensional control target from a plurality of different capture positions via an imaging process utilizing a sensor, where the object includes common surface features, wherein said control target is comprised of rigid lengths of material arranged in three dimensions with respect to the object to provide control features comprising vertices between the rigid lengths;
   (b) measuring the control features from the images of the control target and the object;
   (c) analytically generating a 3-dimensional model of the object by photogrammetrically adjusting the image parameters according to a multiray stereo intersection process by using the measurements of the control features to compute object-space coordinates of any object point which is imaged in the overlapping images from varying capture orientations, thereby providing a photogrammetrically aligned 3-dimensional model of the object that has been processed with an analytical representation of a physical model which represents the imaging process of the sensor that captured the images thereby reducing image errors due to the imaging process including the variable orientations of the capture positions; and
   (d) adjusting the photogrammetrically aligned 3-dimensional model of the object by aligning the common features of the model to like features in the image of the object, thereby producing an aligned dental model from the series of images.

2. The method as claimed in claim 1 wherein step (b) further includes the step of measuring the common features from the series of images of the object.

3. The method as claimed in claim 1 wherein step (c) comprises the steps of:
   performing a photograinmetric adjustment; and
   refining the photogrammetric adjustment by photogrammetrically projecting a 3-dimensional model of the target onto one of the overlapping images of the object, determining misalignment of the control features and correcting the misalignment, thereby producing the photogrammetrically aligned 3-dimensional model of the object.

4. The method as claimed in claim 1 wherein step (d) comprises the steps of:
   determining misalignment of the common features in the photogrammetrically aligned 3-dimensional model relative to the images of the object by photogrammetrically projecting the model onto one of the overlapping images of the object; and
   applying a 3-dimensional morphing algorithm to correct for the misalignment.

5. The method as claimed in claim 1 further comprising the step of using the aligned dental model to generate a dental restorative piece for the intra-oral object.

6. The method as claimed in claim 1 further comprising the steps of providing a database of generic 3-dimensional models and utilizing a selected one of the generic models in step (d) in the alignment of the common features of the photogrammetrically aligned 3-dimensional model to like features on the image of the object.

7. The method as claimed in claim 1 wherein the intra-oral object is one or more teeth.

8. The method as claimed in claim 7 wherein the control target is positioned around said one or more teeth.

9. A system for creating a dental model from a series of overlapping images of an intra-oral object, said system comprising:
   a camera for capturing a series of overlapping images of an intra-oral object and a 3-dimensional control target from a plurality of different capture positions via an imaging process utilizing a sensor, where the object includes common surface features, wherein said control target is comprised of rigid lengths of material arranged in three dimensions with respect to the object to provide control features comprising vertices between the rigid lengths;
   photogrammetric means for measuring the control features from the images of the control target and the object;
   a digital processor including instructions for (a) analytically generating a 3-dimensional model of the object by photogrammetrically aligning the measurements of the control features according to a multiray stereo intersection process to comDute object-space coordinates of any object point which is imaged in the overlapping images from varying capture orientations, thereby providing a photogrammetrically aligned 3-dimensional model of the object that has been processed with an analytical representation of a physical model which represents the imaging process of the sensor that captured the images thereby reducing image errors due to the imaging process including the variable orientations of the capture positions; and (b) adjusting the photogrammetrically aligned 3-dimensional model of the object by aligning the common features of the model to like features in the images of the object, thereby producing an aligned dental model from the series of images.

10. The system as claimed in claim 9 wherein said photogrammetric means further measures the common features from the series of images of the object.

11. The system as claimed in claim 9 wherein said digital processor further includes instructions for performing a photogrammetric adjustment and refining the photogrammetric adjustment by photogrammetrically projecting a 3-dimensional model of the image onto one of the overlapping images of the object, determining misalignment of the control features and correcting the misalignment, thereby producing the photogrammetrically aligned 3-dimensional model of the object.

12. The system as claimed in claim 9 wherein said digital processor further includes instructions for determining misalignment of the common features in the photogrammetrically aligned 3-dimensional model relative to the images of the object by photogrammetrically projecting the model onto one of the overlapping images of the object and applying a 3-dimensional morphing algorithm to correct for the misalignment.

13. The system as claimed in claim 9 further comprising fabrication apparatus using the aligned dental model to generate a dental restorative piece for the intra-oral object.

14. The system as claimed in claim 9 wherein the intra-oral object is one or more teeth.

15. The system as claimed in claim 14 wherein the control target is positioned around said one or more teeth.

16. A method for creating a dental model from a series of overlapping images of one or more teeth, said method comprising the steps of
(a) capturing a series of overlapping images of said one or more teeth and a 3-dimensional control target from a plurality of different capture positions via an imaging process utilizing a sensor, where said one or more teeth include cusp and valley surface features describing their natural topographic surfaces and a rigid control target comprised of rigid lengths of material arranged in three dimensions with resnect to said one or more teeth and resting on said one or more teeth so as to provide control features comprising vertices between the rigid lengths;
(b) measuring the control features from the images of the control target and said one or more teeth;
(c) analytically generating a 3-dimensional model of said one or more teeth by photogrammetrically aligning the measurements of the control features according to a multiray stereo intersection process to compute object-space coordinates of any object point which is imaged in the overlapping images from varying capture orientations, thereby providing a photogrammetrically aligned 3-dimensional model of said one or more teeth that has been processed with an analytical representation of a physical model which represents the imaging process of the sensor that captured the images thereby reducing image errors due to the imaging process including the variable orientations of the capture positions; and
(d) adjusting the photogrammetrically aligned 3-dimensional model of said one or more teeth by aligning the cusp and valley surface features of the model to like features in the images of said one or more teeth, thereby producing an aligned dental model from the series of images.

17. The method as claimed in claim 16 wherein the rigid control target has a saddle form resting over said one or more teeth and the control features comprise vertices in the saddle form.

* * * * *